United States Patent [19]
Zhu et al.

[11] Patent Number: 6,008,055
[45] Date of Patent: Dec. 28, 1999

[54] MODULAR COMPONENT FIBER OPTIC FLUORESCENCE DETECTOR SYSTEM, AND METHOD OF USE

[75] Inventors: Jianzhong Zhu, Omaha, Nebr.; Arthur P. D'Silva, Ames, Iowa

[73] Assignee: Transgenomic, Inc., San Jose, Calif.

[21] Appl. No.: 09/107,830

[22] Filed: Jun. 30, 1998

[51] Int. Cl.$^6$ .................................................. G01N 21/64
[52] U.S. Cl. .................... 436/172; 436/180; 422/82.08; 356/246; 356/344
[58] Field of Search .................................. 436/172, 180; 422/82.07, 82.08; 356/344, 246; 204/452, 603

[56] References Cited

U.S. PATENT DOCUMENTS

| | | | |
|---|---|---|---|
| 3,834,821 | 9/1974 | Ferrari et al. | 356/181 |
| 4,399,099 | 8/1983 | Buckles | 422/58 |
| 4,675,300 | 6/1987 | Zare et al. | 436/172 |
| 4,682,895 | 7/1987 | Costello | 356/402 |
| 4,740,709 | 4/1988 | Leighton et al. | 250/573 |
| 4,837,777 | 6/1989 | Jones et al. | 374/142 |
| 4,844,869 | 7/1989 | Glass | 422/68 |
| 5,068,542 | 11/1991 | Ando et al. | 250/573 |
| 5,078,493 | 1/1992 | Evens et al. | 356/246 |
| 5,096,671 | 3/1992 | Kane et al. | 422/82.07 |
| 5,140,169 | 8/1992 | Evens et al. | 250/576 |
| 5,151,474 | 9/1992 | Lange et al. | 526/60 |
| 5,302,272 | 4/1994 | Klein | 204/299 |
| 5,324,401 | 6/1994 | Yeung et al. | 204/180.1 |
| 5,444,807 | 8/1995 | Liu | 385/125 |
| 5,594,545 | 1/1997 | Saito et al. | 356/246 |

FOREIGN PATENT DOCUMENTS

| | | |
|---|---|---|
| 0089157 | 3/1983 | European Pat. Off. . |
| 9728477 | 12/1996 | WIPO . |

OTHER PUBLICATIONS

Axial–Beam Laser–Excited Fluorescence Detection in Capillary Electrophoresis, Taylor & Yeung, Anal. Chem. 1992, 64.

Laser Fluorescence Detector for Capillary Electrophoresis, Yeung, et al., J. Chromatography, 608 (1992).

Primary Examiner—Jeffrey Snay
Attorney, Agent, or Firm—William B. Walker

[57] ABSTRACT

Systems and methods for inducing and detecting sample analyte(s) identifying fluorescence are disclosed. In particular, a system which includes at least two fiber optic means, within a "throw-away" modular component system component with at least four ports, in which sample analyte fluorescence is caused to occur, by the application of energy to sample analyte(s), is disclosed. The present invention system provides that sample analyte(s) fluorescence inducing energy be entered via an optic fiber means and that produced fluorescence be provided to a detector system via a second optic fiber means. A preferred source of sample analyte(s) fluorescence inducing energy includes lasers, and a preferred method by which to provide sample analyte(s) to the present invention system involves electrophoresis.

26 Claims, 6 Drawing Sheets

MODULAR COMPONENT FIBER OPTIC FLUORESCENCE DETECTOR SYSTEM, AND METHOD OF USE

TECHNICAL FIELD

The present invention relates to systems and methods for inducing and detecting sample analyte(s) identifying fluorescence, and more particularly provides modular component systems, and methods of use thereof, which monitor sample analyte(s) fluorescence. Said systems comprise a fluorescence monitoring fiber optic means present within a disposable sample analyte containing modular component of a sample analysis system in which sample analyte(s) fluorescence is caused to occur by the application of energy thereto, preferably, along a pathway other than parallel to the positioning and orientation of a fiber optic means which carries induced fluorescence to a detector system.

BACKGROUND

The use of fiber optic means to transport electromagnetic wavelengths is well known. In the area of chemical analysis, for instance, various Patents describe the use of fiber optics to carry electromagnetic wavelengths from a source thereof, to a system in which said electromagnetic wavelengths are caused to interact with a sample analyte. As well, various Patents describe the use of fiber optic means to carry said electromagnetic wavelengths which have interacted with said sample analyte to a detecting means. For instance, a Patent to Zare et al., U.S. Pat. No. 4,675,300 describes a method of detecting laser excited fluorescence in an electrokinetic separation system. Said electrokinetic system involved orients a fiber optic means other than axially with respect to an orientation of a flow containing a sample analyte. It is noted that sample analyte flow is effected in the Zare et al. system by application of an electrical potential between a source of sample analyte containing solution, and an outflow container therefore.

A long path flow cell is described in U.S. Pat. No. 5,140,169 to Evens et al. Said Evens et al. system is described as a metal body containing a circular opening at each end extending perpendicularly into a center bore, adapted to receive a sample into the center bore and discharge sample from said center bore. As well, opposing fiber optic probes, each with an external sapphire window which is sealed into said metal body, are present. In use light is piped into one said fiber optic probe, caused to pass axially through said metal body, and exit via said opposing fiber optic probe. Appropriate analysis of a change effected in said light between entry and exit from said metal body allows sample analyte caused to be present in said metal body to be identified.

Another U.S. Pat. No. 5,096,671 to Kane et al., provides that light carrying optical fibers axially enter light to a system which contains a chemical sensor. Axially oriented exiting optical fibers are also present such that in use entered light is caused to interact with said chemical sensor, and then exit therethrough. Interaction with said chemical sensor effects a change in the light between entry thereto and exit therefrom, and chemicals to which the chemical sensor is sensitive affect the properties of the chemical sensor. Said 671 Patent discloses that the sensor can operate utilizing fluorescence. In use the presence of chemicals to which the chemical sensor is sensitive can then be detected.

Another U.S. Pat. No. 4,837,777 to Jones describes a system which utilizes fiber optics to carry light axially into and out of a chamber in which the pressure or temperature can be altered. Changes in light entered to and exiting from said chamber are related to changes in pressure or temperature in said chamber.

A Patent to Buckles, U.S. Pat. No. 4,399,099 describes a system in which an optical fiber is contained in a system into which a fluid is entered. Said fluid causes change in the optical properties of said optical fiber, and detecting changes of light caused to pass therethrough in use, before and after entry of said fluid, is related to the properties of the entered fluid.

U.S. Pat. No. 4,740,709 to Leighton et al., describes a housing with orifices present therein through which liquid is caused to flow in use. An axially oriented light source and a facing sensor are also present. Said system is utilized in measurement of optical density or light scattering measurements in a turbulently entered liquid.

U.S. Pat. No. 4,682,895 to Costello describes a system in which a fiber optic probe carries light into and out of a system. Present within said system is a sample chamber into which sample is entered during use. Said sample chamber essentially comprises a gap in said fiber optic probe pathway. In use light is entered into one end of said fiber optic probe and the light exiting said fiber optic probe is affected by what sample is placed into said sample chamber. The change in light between entry and exit from said fiber optic probe is identifying of said sample.

U.S. Pat. No. 4,844,869 to Glass describes an immunoassay apparatus which employees total internal reflectance of excitation radiation at the interface between an optically conductive rod or fiber and a surrounding liquid. In use radiation is launched onto an unsupported end of a cantelivered rod or fiber and fluorescence radiation tunneling into the unsupported end of the rod or fiber is observed at the same end of the fiber.

U.S. Pat. No. 5,594,545 to Saito et al. describes microflow cell for application in capillary electrophoresis comprising an outer cylinder disposed on the outer periphery of a cylindrical flow cell, with a filling material present between the outer cylinder and the flow cell.

U.S. Pat. No. 5,068,542, to Ando et al., describes use of a fiber optic to intercept axially provided light produced by a laser system. The fiber optics which carry light to a detector involved are not present inside an axially oriented sample containing tube, however. It is noted that the system in Ando et al. does not provide an open ended tube. Either end caps are present on both ends thereof to support liquid inlet and outlet means, or one end thereof is closed with an optical fiber secured therein and the other end thereof has an end cap thereon.

U.S. Pat. No. 5,068,542 to Ferrari et al. describes a system in which end caps affixed to a tube contain light fibers which both carry light from a source thereof, and to a detector. It is noted that the system in Ferrari et al. does not provide an open ended tube, in that end caps are present on both ends thereof to support present fiber optic means.

Patents which arguably describe modular elements from which project ports are U.S. Pat. No. 5,078,493 to Evens et al.; U.S. Pat. No. 5,151,474 to Lange et al.; U.S. Pat. No. 5,302,272 to Klein and PCT Application No. WO 97/28477. However, none of said references identify use in a sample analyte identifying fluorescence inducing system.

Also, it is noted that two additional U.S. Pat. No. 5,068,542 to Ando et al. and U.S. Pat. No. 3,834,821 to Ferrari et al. describe the presence of optical fibers which extend only a short distance into the effective systems thereof, (ie. into end caps (116) & (114) in Ferrari et al. and into tube (1) of Ando et al. This is beneficial to operation of the both the 542 and 821 Patent Inventions as fluid flow through the respective tubes is not blocked or impeded by optical fibers in use.

Finally, a paper by Yeung et al, titled "Laser Fluorescence Detector For Capillary Electrophoresis", J. Chromatography, 608(1992), 73–77, describes a laser-based fluorometer for use in detection in capillary electrophoresis. While laser induced fluorescence, in combination with electrophoresis mediated provision of sample analyte into the described system is reported to be a very efficient approach to sample analyte identification, the use of axially oriented optical fibers in a system for detection of sample analyte identifying fluorescence is not described.

The above discussion of known Patents and Articles shows that while the use of optical fibers in systems for use in sample analysis is known, no known system or method provides that axially oriented fiber optic means should be present within at least a majority of an axially oriented modular component of a sample analysis system in which sample analyte fluorescence is caused to occur by the application of energy to a present sample analyte. This is particularly true where fluorescence inducing energy is entered along a pathway other than parallel to a longitudinal direction of a system for use in sample analysis, and where sample analyte investigated is caused to enter a modular component of a sample analysis system by electrophoresis. Neither does any known system or method describe use of a system with at least four ports, each of which ports projects from a common volume, two of said ports having the fiber optic means present therein, and two of which provide access to sample analyte containing sample solution. The present invention provides such systems and methods of its use.

DISCLOSURE OF THE INVENTION

Prior to presenting the present invention modular component fiber optic fluorescence detector system, and method of use, it is noted that a previously reported axially oriented system, (which was subject in patent application Ser. No. 08/662,467, now U.S. Pat. No. 5,763,277), comprises a modular component with an axially oriented system component bore therethrough, and further comprises a fiber optic means, an axially oriented end of said fiber optic means being present within said axially oriented system modular component bore. During use, sample analyte fluorescence is caused to occur by the application of energy to sample analyte(s) caused to be present within said axially oriented system modular component bore, with said fluorescence inducing energy being entered to said axially oriented system modular component bore along a path which is other than essentially parallel to said axially oriented system axial orientation. Produced fluorescence enters said axially oriented end of said fiber optic means present within said axially oriented system modular component bore, and is transmitted by said fiber optic means to a detector system located distally along said fiber optic means.

Continuing, the axially oriented system modular component reported in patent application Ser. No. 08/662,467, (now U.S. Pat. 5,763,277) is typically essentially tubular in shape with means for entry of sample analyte, (typically in a solution form), present, typically, at ends thereof. In addition, it is noted that the entire, previously reported, axially oriented system modular component can be transparent to fluorescence producing energy, or only a window in said axially oriented system component might be transparent to fluorescence producing energy. In the later case said transparent window is located such that fluorescence producing energy entered therethrough is provided to said axially oriented system modular component near the location of the axially oriented end of said fiber optic means present in said axially oriented system modular component bore.

A preferred embodiment of said previously reported axially oriented system modular component further comprises a sample solution containing system source of sample analyte(s) and a sample solution receiving system. In use said axially oriented system modular component bore is caused to be filled with a sample analyte(s) containing sample solution, and sample analyte(s) containing sample solution present at one end of said axially oriented system modular component is caused to be continuous with a sample analyte containing sample solution present in said sample solution containing system source of sample analyte, while sample analyte(s) present at an axially distal end of said axially oriented system modular component is caused to be continuous with sample analyte containing sample solution present in said sample solution receiving system. Said configuration, it will be appreciated is appropriate for use in an electrophoresis scenario wherein an electric potential is applied between said sample analyte containing solution in said sample solution containing system source of sample analyte and a sample solution receiving system, such that sample analyte(s) present therein are caused to migrate through said axially oriented system modular component bore.

A method of producing and accessing for analysis, sample analyte identifying fluorescence can involve:

a. providing an axially oriented system modular component as described infra;

b. causing sample analyte(s) to be present in said axially oriented system modular component bore;

c. causing sample analyte(s) fluorescence inducing energy to be entered to said axially oriented system modular component along a path which is other than essentially parallel to said modular component axial orientation;

such that produced fluorescence enters said axially oriented end of said fiber optic means present within said axially oriented system modular component, and is transmitted by said fiber optic means to a detector system located distally along said fiber optic means.

Said described method of producing and accessing for analysis, sample analyte identifying fluorescence, in a preferred embodiment, provides that the step c. act of causing sample analyte(s) fluorescence inducing energy enter said fluorescence inducing energy along a path which is essentially perpendicular to said axially oriented system modular component axial orientation.

A more detailed method of producing, and accessing for analysis, sample analyte identifying fluorescence, applicable in an electrophoresis setting, comprises the steps of:

a. providing an axially oriented system modular component as described infra, including said sample solution containing system source of sample analyte(s), and a sample solution receiving system;

b. causing a sample analyte(s) containing sample solution to be continuously present within said axially oriented system modular component bore, said sample solution containing system source of sample analyte(s) and said sample solution receiving system;

c. applying an electric potential between sample analyte(s) containing sample solution present in said sample solution containing system source of sample analyte(s) and said sample solution receiving system;

d. causing sample analyte(s) fluorescence inducing energy to be entered to said axially oriented system component along a path which is other than essentially parallel to said modular component axial orientation;

such that produced fluorescence enters said axially oriented end of said fiber optic means present within said axially oriented system modular component, and is transmitted by said fiber optic means to a detector system located distally along said fiber optic means.

Again, said described method of producing and accessing for analysis, sample analyte identifying fluorescence, in a preferred embodiment, provides that, the step d. act of causing sample analyte(s) fluorescence inducing energy enter said fluorescence inducing energy along a path which is essentially perpendicular to said axially oriented system modular component axial orientation.

A preferred source of sample analyte fluorescence inducing energy should be understood to include laser systems.

While the discussion infra herein describes a previously reported, utility providing, system for producing and accessing sample analyte identifying fluorescence, problems have been encountered in its application. For instance, in practice it can be somewhat difficult to mount a fiber optic means through an axially oriented system modular component bore, and to maintain a sample analyte flow path in an axial bore when a fiber optic means is randomly threaded therethrough. In addition, it can be very difficult to wash-out such a system between samples. A preferable system was disclosed in pending patent application Ser. No. 08/753,978 filed Dec. 4, 1996, and provides "throw-away" modular components which can easily be attached and removed from a modular component system for use in inducing and measuring sample analyte identifying fluorescence.

In said patent application Ser. No. 08/753,978 filed Dec. 4, 1996, the invention is a modular component system for use in inducing and measuring sample analyte identifying fluorescence, said modular component system comprising a component with at least four ports. Said modular component system further comprises at least first and second fiber optic means present in, respectively, at least the first and second of said at least four ports. During use, sample analyte containing solution is caused to be continuously present in and between said third and forth ports thereof, and sample analyte fluorescence is caused to occur by the application of energy to sample analyte(s) caused to be present within said modular component system. Said fluorescence inducing energy is entered to said modular component system via one of said first and second fiber optic means, such that produced fluorescence enters the remaining said second and first fiber optic means, respectively, and is transmitted by said remaining second or first fiber optic means to a detector system located distally along said remaining second and first fiber optic means, respectively.

One preferred embodiment of the modular component system modular component with at least four ports provides that said at least four ports be oriented in an essentially cross shape, with means for entry of sample analyte present at two ports thereof. In said embodiment, preferably, all present ports are present in a common plane. As well, it is preferred, but not required, that each of said four ports projects at an essentially ninety degree angle with respect to each of the other of said at least four ports.

Another preferred embodiment of the modular component system modular component with at least four ports provides three of said ports in an essentially "tee" shape, with a forth port projecting out of a plane formed by said essentially "tee" shape forming three ports. In this embodiment, preferably, but not necessarily, said forth port projects essentially perpendicularly to the plane formed by said three "Tee" shape forming ports which preferably form a common plane. Again, it is preferred that each of said four ports projects at an essentially ninety degree angle with respect to each of the other of said at least four ports.

As described infra herein with respect to the previously reported axially oriented bore system, a present invention modular component system for use in inducing and measuring sample analyte identifying fluorescence further comprises a sample solution containing system source of sample analyte(s) and a sample solution receiving system. In use said modular component system component with at least four ports is caused to be filled with a sample analyte(s) containing sample solution, and such that sample analyte(s) containing sample solution present at said source of sample analyte(s) is caused to be continuous with a sample analyte containing sample solution present in said sample solution receiving system. Said continuity being via said third and forth ports. Again, in use an electric potential is applied between said sample analyte containing solution in said sample solution containing system source of sample analyte and a sample solution receiving system, such that sample analyte(s) present therein are caused to migrate through said modular component system.

A method of producing and accessing for analysis, sample analyte identifying fluorescence utilizing the present invention modular component system then comprises the steps of:

a. providing a modular component system for use in inducing and measuring sample analyte identifying fluorescence as described infra herein;

b. causing sample analyte(s) to be continuously present in said modular component system component with at least four ports, between said third and forth ports;

c. causing sample analyte(s) fluorescence inducing energy to be entered to said modular component system component with at least four ports via one of said first and second fiber optic means;

such that produced fluorescence enters said modular component system component with at least four ports fiber optic means present within one of said second and first ports respectively, and is transmitted by said fiber optic means to a detector system located distally along said fiber optic means.

A preferred source of sample analyte fluorescence inducing energy should be understood to include laser systems in performing step c.

A more detailed method of producing, and accessing for analysis, sample analyte identifying fluorescence, applicable in an electrophoresis setting, comprises the steps of:

a. providing a present invention modular component system as described infra, including said sample solution containing system source of sample analyte(s), and a sample solution receiving system;

b. causing sample analyte(s) to be continuously present in said modular component system component with at least four ports, between said third and forth ports;

c. applying an electric potential between sample analyte(s) containing sample solution present in said sample solution containing system source of sample analyte(s) and said sample solution receiving system;

d. causing sample analyte(s) fluorescence inducing energy to be entered to said modular component system component with at least four ports via one of said first and second fiber optic means;

such that produced fluorescence enters said modular component system component with at least four ports fiber optic means present within one of said second and first ports respectively, and is transmitted by said fiber optic means to a detector system located distally along said fiber optic means.

A preferred source of sample analyte fluorescence inducing energy should be understood to include laser systems in performing step d.

With the foregoing serving as an introduction, it is disclosed that another preferred embodiment of the present invention modular component system for use in inducing and measuring sample analyte identifying fluorescence was first disclosed in patent application Ser. No. 890,974 and comprises a modular component which is an essentially tubular shaped element with an outer wall and two ends, one end of said essentially tubular shaped element being open and the other end thereof being essentially closed. Said essentially closed end has a fiber optic means for carrying induced fluorescence to a detector system secured therewithin, with said fiber optic means for carrying induced fluorescence to a detector system projecting from outside said essentially tubular shaped element into said essentially tubular shaped element, through a securing interface means, and further projecting through at least a majority of the length of a space bounded by said outer wall and between said open and essentially closed ends of said essentially tubular shaped element, such that a substantially annular space is formed inside said essentially tubular shaped element and around said fiber optic means for carrying induced fluorescence to a detector system. (Note, said substantially annular space can be formed during manufacture where tolerances can be monitored). Said substantially annular space formed around said fiber optic means for carrying induced fluorescence to a detector system is accessed at a location between said open end and said essentially closed end of said essentially tubular shaped element by an annular space accessing means which projects through said outer wall of said essentially tubular shaped element. Said modular component system further comprises an essentially transparent essentially tubular connection means as either an integral part of, or attached to said open end of said essentially tubular shaped element. During use fluorescence inducing energy is caused to be entered thereinto through an essentially transparent wall of said essentially transparent essentially tubular connection means wherein it interacts with sample analyte caused to be present in said essentially transparent essentially tubular connection means. Resulting induced fluorescence is intercepted by an end of said fiber optic means for carrying induced fluorescence to a detector system present in said essentially tubular shaped element, and transmission to a detector system is mediated thereby. Said modular component system for use in inducing and measuring sample analyte identifying fluorescence can further comprise a source of fluorescence inducing energy, said source of fluorescence inducing energy being positioned and oriented with respect to said essentially transparent essentially tubular connection means so as to provide fluorescence inducing energy through said essentially transparent wall thereof along a pathway oriented other than parallel to the orientation of said fiber optic means for carrying induced fluorescence to a detector system present in said essentially tubular shaped element. Typically, said source of fluorescence inducing energy is a laser system. Said modular component system for use in inducing and measuring sample analyte identifying fluorescence, can further comprise a source of sample analyte(s) containing sample solution system, and a sample solution receiving system, such that sample analyte(s) containing sample solution present in said source of sample analyte(s) containing sample solution system, is caused to be continuous with a sample analyte(s) containing sample solution present in said sample solution receiving system sequentially through said [said] essentially transparent essentially tubular connection means and said essentially tubular shaped element and said annular space accessing means; such that in use an electric potential is applied between said sample analyte(s) containing solution in said sample solution containing system source of sample analyte(s) containing sample solution system, and said sample analytes containing sample solution present in said sample solution receiving system, with the result being that sample analyte(s) are caused to migrate into said modular component system for use in inducing and measuring sample analyte identifying fluorescence via said essentially transparent essentially tubular connection means and said open end of said essentially tubular shaped element, then through said annular space formed around said fiber optic means for carrying induced fluorescence to a detector system, and out of said essentially tubular shaped element annular space via said annular space accessing means under the influence of a resulting electric field.

In contrast to said prefered embodiment of the present invention system, previously known modular components with a fiber optics means containing axially oriented system component therein, and which further comprise an axially oriented system component internal volume accessing means through a wall of said axially oriented system component, (rather than through an open end of an axially oriented system component "bore"), provide that the fiber optic means be present in less than a majority of the length of the axially oriented system component internal volume. In said known prior systems a limited length of fiber optic means present inside a system "bore" (or tube or the like), provides utility by not blocking fluid flow therethrough. Where electrophoresis is utilized as a sample analyte driving force, as in the preferred embodiment of the present invention however, fluid flow is less a concern and the presence of a fiber optic means within and over a majority of the length of an axially oriented system modular component internal volume does not significantly degrade utility.

A method of producing and accessing for analysis, sample analyte identifying fluorescence comprises the steps of:

a. providing a modular component system for use in inducing and measuring sample analyte identifying fluorescence as just described.

b. causing sample analyte(s) to be continuously present in said modular component system component;

c. causing sample analyte(s) fluorescence inducing energy to be entered to said essentially transparent essentially tubular connection means through said essentially transparent wall thereof;

such that produced fluorescence enters said fiber optic means and is transmitted by said fiber optic means to a detector system located distally along said fiber optic means.

A preferred source of sample analyte(s) fluorescence inducing energy involves the use of lasers and energy is caused to be entered through said essentially transparent essentially tubular connection means.

A more detailed method of producing and accessing for analysis, sample analyte identifying fluorescence comprising the steps of:

a. providing a modular component system for use in inducing and measuring sample analyte identifying fluorescence as just described.

b. causing sample analyte(s) to be continuously present in said sample solution containing system source of sample analyte(s) and said essentially transparent essentially tubular connection means and said essentially tubular shaped element and said sample solution receiving system;

c. applying an electric potential between sample analyte(s) containing sample solution present in said sample solution containing system source of sample analyte(s) and said sample solution receiving system;

d. causing sample analyte(s) fluorescence inducing energy to be entered to through said essentially transparent essentially tubular connection means;

such that produced fluorescence enters said fiber optic means and is transmitted by said fiber optic means to a detector system located distally along said fiber optic means.

A preferred source of sample analyte(s) fluorescence inducing energy again involves the use of lasers and energy is caused to be entered through said essentially transparent essentially tubular connection means.

The present invention system will be better understood by reference to the Detailed Description Section of this Disclosure, with reference being had to the accompanying Drawings.

SUMMARY OF THE INVENTION

It is a primary purpose of the present invention to provide modular component systems and methods of use thereof, for inducing and detecting sample analyte(s) identifying fluorescence.

It is a particular purpose of the present invention to disclose a system which includes a fiber optic means, and is a modular component system in which sample analyte fluorescence is caused to occur, by the application of energy to present sample analyte(s) is disclosed along a pathway other than parallel to the longitudinal direction of said fiber optic means.

It is yet another particular purpose of the present invention to disclose that sample analyte(s) fluorescence inducing energy should be directed from the system of the present invention into a detector system, via fiber optic means.

It is still yet another purpose of the present invention to teach that a preferred source of sample analyte(s) fluorescence inducing energy includes lasers.

It is yet still another purpose of the present invention to describe that a preferred method by which to provide sample analyte(s) to the present invention system involves electrophoresis.

It is still another purpose of the present invention to describe a modular component system which allows for easy sample change by change of a disposable modular component.

BRIEF DESCRIPTION OF THE DRAWINGS

FIGS. 9a1, 9a2, 9b and 9c show another preferred embodiment of a present invention modular component system component with at least four ports.

FIG. 10 shows a present invention modular system with the modular component system component of FIGS. 9a1, 9a2, 9b and 9c mounted therein.

DETAILED DESCRIPTION

Figure 1:
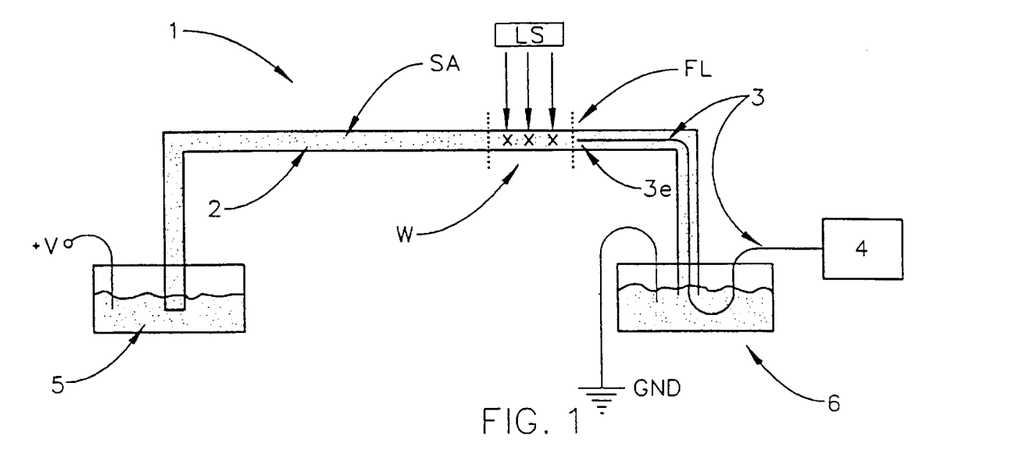
FIG. 1 shows a modular axially oriented system component, including an axially oriented fiber optic means.
Figure 2:
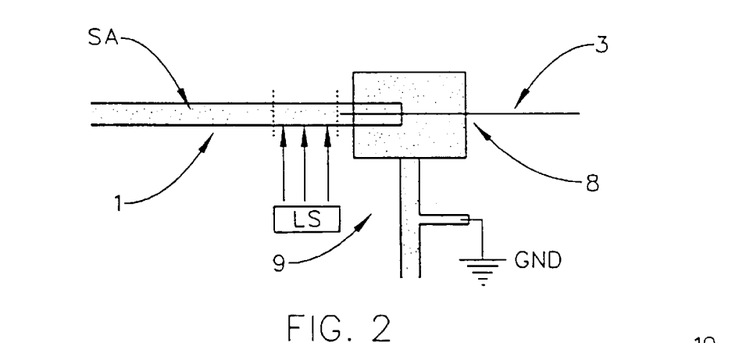
FIG. 2 shows an axially oriented optical fiber means axially entered to a modular axially oriented system component, via a sealed or sealable means.

Turning now to the Drawings, there is shown in FIG. 1a axially oriented system modular component (1) for use in inducing and measuring sample analyte (SA) identifying fluorescence (FL). Said axially oriented system modular component (1) comprises an axially oriented system bore (2) therethrough, and further comprises a fiber optic means (3), an axially oriented end (3e) of which fiber optic means (3) is present within said axially oriented system modular component bore (2). It should be noted that said fiber optic means (3) is threaded into the axially oriented system modular component bore (2) from an open right oriented side thereof, through which sample solution flows in use. This demonstrates a preferred axially oriented system component embodiment. However, as shown in FIG. 2, it is to be understood that said axially oriented fiber optic means (3) could be entered through a sealed or sealable opening (8) in a retaining means (9) for said axially oriented system modular component (1), such that said fiber optic means (3) is entered thereto directly in line with said axially oriented system modular component bore (2). Such a configuration is within the scope of the present invention.

Referring again to FIG. 1, during use, sample analyte fluorescence (FL) is caused to occur by the application of energy from source (LS) to sample analyte(s) (SA) which are caused to be present within said axially oriented system modular component bore (2), with said fluorescence (FL) inducing energy, (LS) being entered to said axially oriented system modular component bore (2) along a path which is other than essentially parallel to said axially oriented system modular component (1) axial orientation. Produced fluorescence (FL) enters said axially oriented end (3e) of said fiber optic means (3) present within said axially oriented system modular component bore (2), and is transmitted by said fiber optic means to a detector system (4) located distally along said fiber optic means (3).

The described axially oriented system modular component (1) is typically essentially tubular in shape with means for entry of sample analyte, (SA), typically in a solution form, present at ends thereof. In addition, it is noted that the entire axially oriented system modular component (1) can be transparent to fluorescence (FL) producing energy (LS), or only a window (W) in said axially oriented system modular component (1) might be transparent to fluorescence (FL) producing energy from source (LS). In the later case said transparent window (W) is located such that fluorescence (FL) producing energy (LS) entered therethrough is provided to said axially oriented system modular component (1) near the location of the axially oriented end (3e) of said fiber optic means (3) present in said axially oriented system modular component bore (2).

A preferred embodiment of the described axially oriented system further comprises a sample solution containing system source of sample analyte(s) (5) and a sample solution receiving system (6). In use said axially oriented system modular component bore (2) is caused to be filled with a sample analyte(s) (SA) containing sample solution, and sample analyte(s) (SA) containing sample solution present at one end of said axially oriented system modular component (1) is caused to be continuous with a sample analyte containing sample solution present in said sample solution containing system source of sample analyte (5), while sample analyte(s) present at an axially distal end of said axially oriented system modular component (1) is caused to be continuous with sample analyte containing sample solution present in said sample solution receiving system (6). Said configuration, it will be appreciated is appropriate for use in an electrophoresis scenario wherein an electric potential (V+) is applied to said sample analyte containing solution in said sample solution containing system source of sample analyte (5) and a ground potential (GND) is applied to said sample solution receiving system (6), such that sample analyte(s) (SA) present therein are caused to migrate through said axially oriented system component bore (2). Sample analytes will be caused to transverse the length of the axially oriented system modular component (1) at rates dependent upon, for instance, charge and mass thereof.

Figure 3:
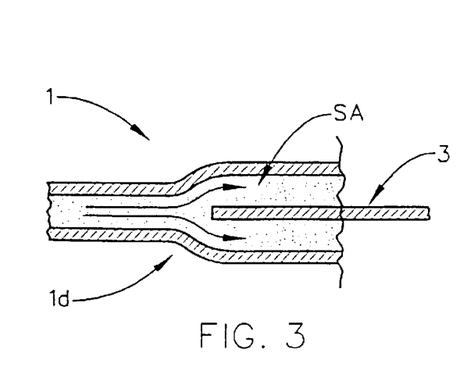
FIG. 3 shows an shows a modular axially oriented system component, including an axially oriented fiber optic means, in which the inner diameter of the modular axially oriented system component is increased at the location of contained axially oriented fiber optic means.

FIG. 3 shows that the axially oriented system modular component (1) can provide an increased inner diameter (1d) at the point at which the fiber optic means (3) enters thereto. Said increased inner diameter (1d) provides a non-constricted annular space in which sample analyte (SA) containing sample solution (5) can flow, in the presence of said fiber optic means (3).

Figure 4:
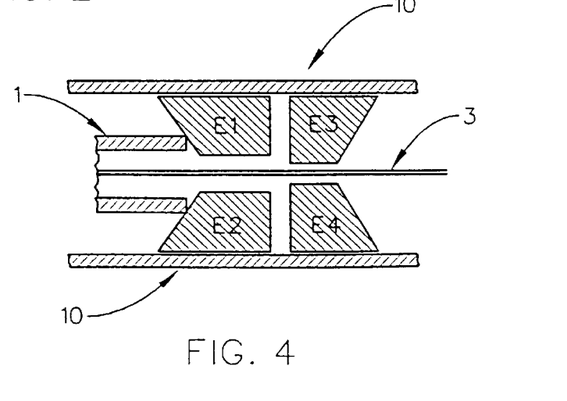
FIG. 4 shows an alignment system means by which the modular axially oriented system component and the fiber optic means can be easily aligned in use.

FIG. 4 shows an alignment system means by which the axially oriented system modular component (1) and the fiber optic means (3) can be easily aligned in use. Shown are elements (E1), (E2), (E3) & (E4). Each of said elements presents with an angled surface which in use is caused to face the entry of the axially oriented system modular component (1) or the fiber optic means (3), by position retention mounting in securing means (10). Note that angled surfaces of elements (E1) & (E2) provide centering of an axially oriented system modular component (1) entered thereto, and angled surfaces of elements (E3) & (E4) provide centering means for fiber optic means (3) entered thereto. Note that the centering effect of elements (E3) & (E4) provides the fiber optic means (3) centrally in the axially oriented system modular component (1). That is, the vertically shown length of element (E4) is greater than that of element (E2). In use a user can then easily enter fiber optic means (3) to axially oriented system modular component (1) by simple laterally imposed motion of each, as viewed in FIG. 4.

Note, it is to be understood that terminology "axially oriented" can mean a capillary tube with an inner "bore" diameter on the order of, for instance, approximately one-hundred (100) microns, and the terminology "fiber optic means" can mean an accompanying electromagnetic wavelength transmitting means with an outer diameter of, for instance, seventy-five (75) microns diameter or less.

With the foregoing disclosure in mind, it should be realized that while the discussion infra herein describes a utility providing system for producing and accessing sample analyte identifying fluorescence, problems have been encountered in its application. In practice it can be difficult to thread a fiber optic means through an axially oriented bore, and to maintain a sample analyte flow path in an axial bore when a fiber optic means is threaded therethrough. In addition, it can be difficult to wash-out such a system between samples. A preferable system would provide "throw-away" modules which can easily be attached and removed from a modular component system for use in inducing and measuring sample analyte identifying fluorescence.

Figure 5:
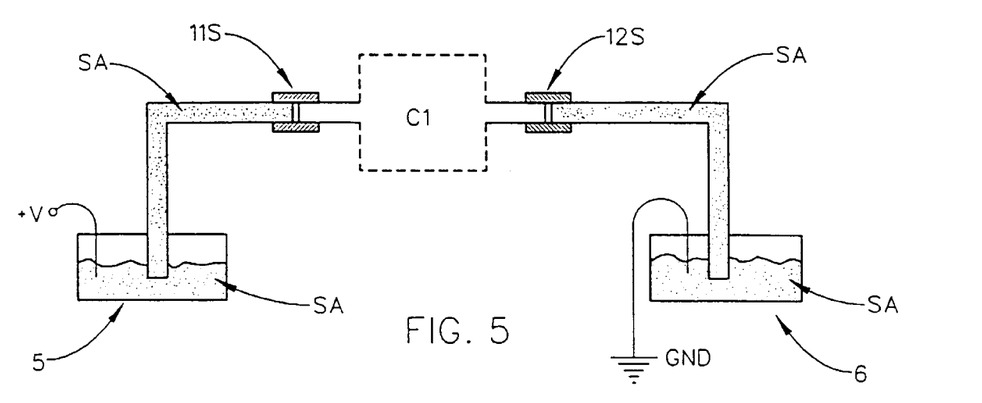
FIG. 5 shows a modular component system of the present invention.
Figure 7:
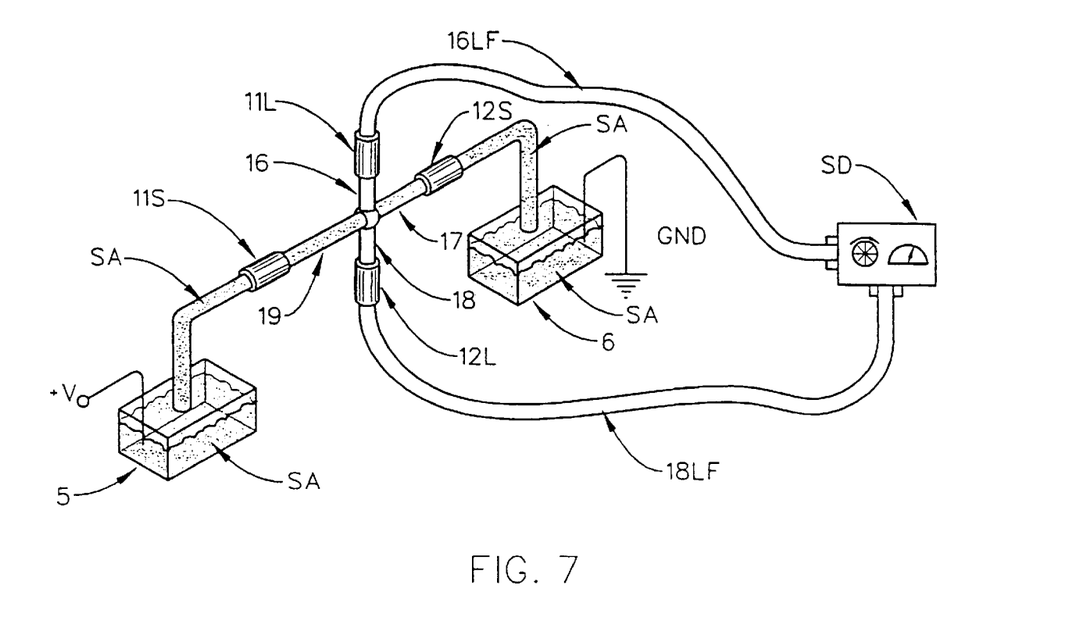
FIG. 7 shows a present invention modular system with the modular component system component of FIGS. 6a, 6b and 6c mounted therein.
Figure 8:
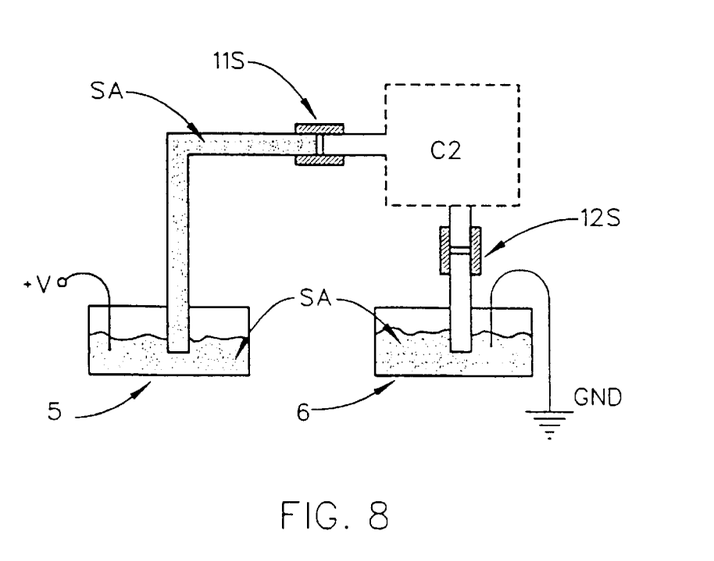
FIG. 8 shows a modular component system of the present invention.

Proceeding, FIGS. 5 and 8 show present invention modular component systems comprised of a source of sample solution containing system source of sample analyte(s) (5) and a sample solution receiving system (6). Shown as coupled to said modular component systems, via connectors (11s) & (12s), are modular component system components identified as (C1) in FIG. 5 and as (C2) in FIG. 8. Said modular component system component (C1) is better shown in FIGS. 6a, 6b, 6c, 6d & 7, while modular component system component (C2) is better shown in FIGS. 9a1, 9a2, 9b, 9c & 10.

Figure 6A:
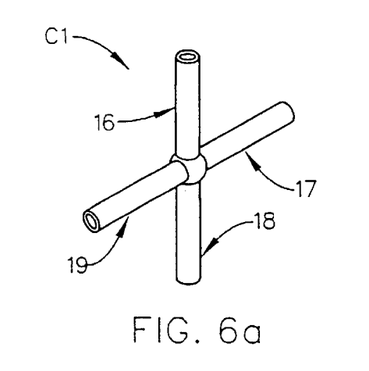
FIGS. 6a, 6b and 6c show one preferred embodiment of a present invention modular component system component with at least four ports with two present fiber optic means placed at one-hundred-eighty degrees with respect to one another.
Figure 6B:
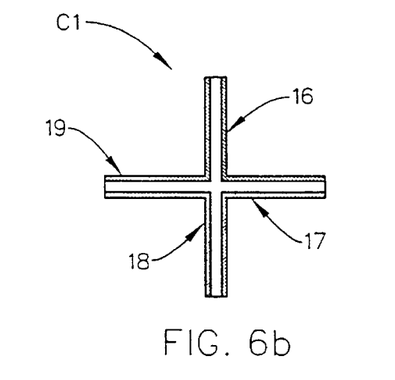
Figure 6C:
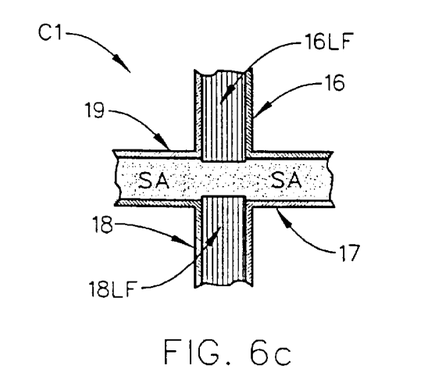
Figure 6D:
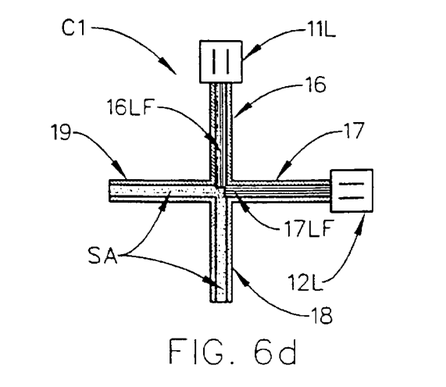
FIG. 6d show the preferred embodiment of FIGS. 6a, 6b and 6c two present fiber optic means placed at ninety degrees with respect to one another.

The preferred embodiment of the modular component system modular component (C1) is shown to be comprised of at least four ports in FIGS. 6a, 6b, 6c, 6d and 7 and provides that said four ports (16), (17), (18) & (19) be oriented in an essentially cross shape, with means for entry of sample analyte present at two ports thereof. In said embodiment, preferably, all present ports are in a common plane. As well, it is preferred that each of said four ports projects at an essentially ninety degree angle with respect to each of the other of said at least four ports. FIG. 6c shows optic fiber means (16LF) and (18LF) present at one-hundred-eighty (180) degrees with respect to one another, and FIG. 6d shows optic fiber means (16LF) and (17LF) present at ninety (90) degrees with respect to one another. FIG. 6d shows connectors (111) & (121) are present for securing optic fiber means (16LF) and (17LF) in place for use in a system such as shown in FIG. 7, but wherein Sample Analyte (SA) flows through a ninety (90) degree bend in use, rather than straight through a Modular Component (C1) as actually shown in FIG. 7.

The preferred embodiment of the modular component system modular component (C2) is shown to be comprised of at least four ports in FIGS. 9a1, 9a2, 9b, 9c and 10 provides three ports (16) (17) & (19) in an essentially "tee"

shape, with a forth port (18) (18'), projecting out of a plane formed by said essentially "tee" shape forming three ports. In this embodiment, preferably said forth port (18) (18') projects essentially perpendicularly to the plane formed by said three "Tee" shape forming ports which form a common plane. Again, it is preferred that each of said four ports projects at an essentially ninety degree angle with respect to each of the other of said at least four ports.

Figure 9A:
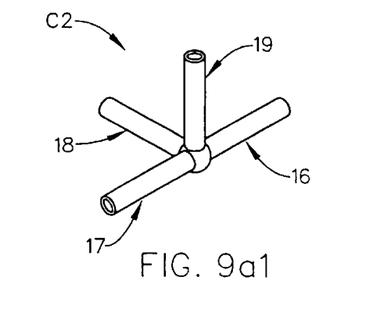
Figure 9A:
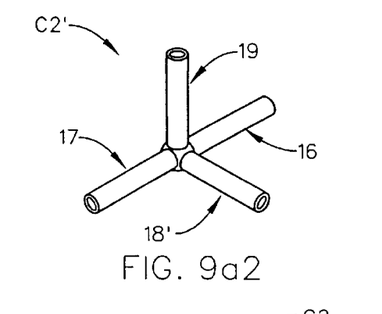
Figures 9B, 9C, 10:
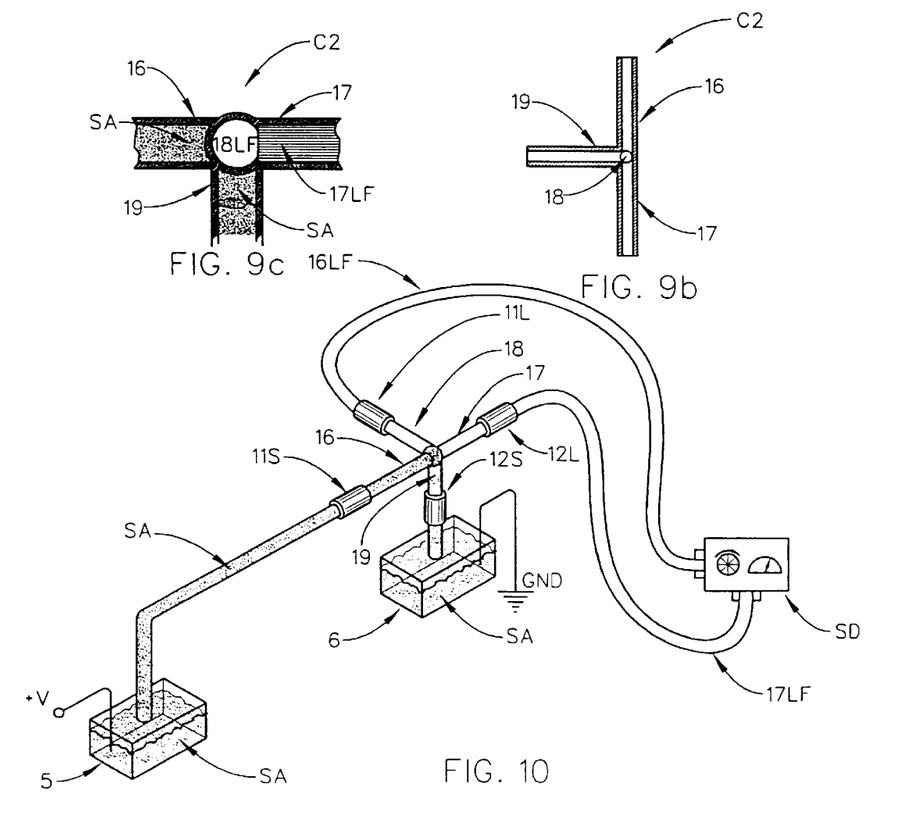

Turning now to FIGS. 7 and 10, it will be appreciated that a preferred embodiment of the present invention is a modular component system for use in inducing and measuring sample analyte identifying fluorescence, said modular component system comprising a component with at least four ports. FIG. 7 shows a first preferred embodiment (C1) and FIG. 10 a second preferred embodiment (C2) of modular component system comprising a component with at least four ports (16), (17), (18), & (19). Said modular component system further comprises at least first and second fiber optic means, (see (16LF) & (18LF) in FIG. 7 and (16LF) & (17L) in FIG. 10), present in, respectively, at least first and second, (see (16) & (18) in FIG. 7 and (18) & (17) in FIG. 10), of said at least four ports. During use, sample analyte (SA) containing solution is caused to be continuously present between third and forth ports, (see (19) & (17) in FIG. 7 and (16) & (19) in FIG. 10), thereof and sample analyte fluorescence is caused to occur by the application of energy to sample analyte(s) (SA) caused to be present within said modular component system identified as (C1) in FIG. 7 and (C2) in FIG. 10. Said fluorescence inducing energy is entered to said modular component system via one of said first and second fiber optic means, such that produced fluorescence enters the remaining said second and first fiber optic means, respectively, and is transmitted by said remaining second and first fiber optic means to a detector system located distally along said remaining second and first fiber optic means, respectively.

Note that, as best indicated in FIG. 6c, where an optic fiber means (16LF) (18LF) is present in a port (16) (18), it is to be to understood that the fit between the outer surface of a fiber optic means and the inner surface of a port is caused to be "liquid tight". That is, sample analyte (SA) in liquid media, which is continuously present in ports (19) (17) is not able to enter ports (16) (18).

As described infra herein with respect to the axial bore system, the present invention modular component system for use in inducing and measuring sample analyte identifying fluorescence further comprises a sample solution containing system source (5) of sample analyte(s) (SA) and a sample solution receiving system (6). In use said modular component system component with at least four ports, (C1), (C2) is caused to be filled with a sample analyte(s) containing sample solution (SA), and such that sample analyte(s) containing sample solution present at said source of sample analyte(s) (5) is caused to be continuous with a sample analyte containing sample solution present in said sample solution receiving system (6). Said continuity being via third and forth ports, (see (19) & (17) in FIG. 7 and (16) & (19) in FIG. 10). Again, in use an electric potential (+V) is applied between said sample analyte containing solution in said sample solution containing system source of sample analyte and a sample solution receiving system, (which is shown at ground (GND) potential), such that sample analyte(s) (SA) present therein are caused to migrate through said modular component system (C1), (C2).

It is further noted that in FIGS. 7 and 10 connectors (11L) and (12L) serve to indicated that fiber optic means, (see (16LF) & (18LF) in FIG. 7 and (16LF) & (17LF) in FIG. 10), are held positioned within first and second ports, (see (16) & (18) in FIG. 7 and (18) & (17) in FIG. 10). FIGS. 6c and 9c show said fiber optic means present in said first and second ports. It is also to be understood that the first and second ports are essentially interchangable, as are the third and forth ports. (As well, in the preferred embodiment, any of said at least four ports can constitute any of the identified first, second, third and forth ports as it is the relative positioning of and function performed by said ports which is important, with inner diameters being preferably, but not necessarily the same in any of said first, second, third and forth ports). In use it is important only that:

a. fluorescence exciting energy is made available to sample analyte (SA), via either the first or second port and that fluorescence developed be detected via fiber optic means present in the other of said second and first ports respectively; and b. that sample analyte (SA) be present in a liquid media which is continuous between source of sample solution containing system source of sample analyte(s) (5) and a sample solution receiving system (6), via the third and forth ports.

FIGS. 7 and 10 each also show a Source and Signal Detector (SD) into which the fiber optic means (16LF) & (18LF) in FIG. 7, and (16LF) & (17LF) in FIG. 10 are attached. In use one attached optic fiber means will carry fluorescence exciting energy from said Source and Signal Detector (SD) to the location of a sample analyte (SA), and one will carry electromagnetic radiation of a sample analyte (SA) fluorescence effected wavelength therefrom, to said Source and Signal Detector (SD).

It is also noted that additional ports could be present in either the (C1) or (C2) embodiments. For instance, additional fiber optic means containing ports could be present.

Methods of producing and accessing for analysis, sample analyte identifying fluorescence utilizing the present invention modular component systems components (C1), (C2) as shown in FIGS. 7 and 10 were described in the Disclosure of the Invention Section.

It is noted that in the modular component system of FIG. 7, the sample analyte (SA) fluorescence exciting electromagnetic energy is entered and exited via, for instance, first and second ports (16) & (19) respectively, which first and second ports are oriented such that entered electromagnetic energy from said first port (16) contained fiber optic means (16LF) will directly enter second port (18) contained fiber optic means (18LF). In use a filter, (not shown), will normally be present in the Source and Signal Detector (SD), to eliminate any but sample analyte (SA) fluorescence effected wavelengths from being detected.

It is to be understood that preferred sources of fluorescence (FL) producing energy (LS) in a Source and Signal Detector (SD), include laser systems.

It is to be understood that the terminology "essentially tubular" can include tube shapes other than circular cross-sections. It is also noted that while the Figures show essentially circular optic fiber means, and ports, any functional shape therefore is to be considered as within the scope of the present invention.

It is also to be understood that generally first and second ports (16) & (18) in a FIG. 7 (C1), and (18) & (17) in a FIG. 10 (C2), modular component system component with at least four ports, can be functionally interchanged, as can be third and forth ((19) & (17) in FIG. 7 and (16) & 19) in FIG. 10), in use. That is, all said at least four ports (16), (17), (18) & (19) access a centrally located common internal volume.

It is also to be understood that a FIG. 9a2 modular component system component with at least four ports (C2)

embodiment can be used in place of the FIG. 9a1 (C2) embodiment in FIG. 10, or either FIG. 9a1 or 9a2 modular component system component with at least four ports (C2) could be placed into the modular component system of FIGS. 5 and 7, as could the FIG. 6a modular component system component with at least four ports (C1) embodiment be placed into the modular component system of FIGS. 8 and 10. Were the later done, it should be apparent that ports (19) and (18), for instance, could be positioned to carry sample analyte (SA), (instead of (19) & (17)), with the fiber optic means (16LF) and (18LF) being placed into the remaining ports (16) & (17). That is, in generally, in use, fiber optic means can be placed into any two ports of a (C1) or (C2) modular component, with sample analyte (SA) then being caused to be present in remaining ports. That is, the present invention utility derives primarily from the presence of "throw-away" modular components (C1) (C2) in the systems of FIGS. 5, 7, 8 and 10.

Figure 11A:
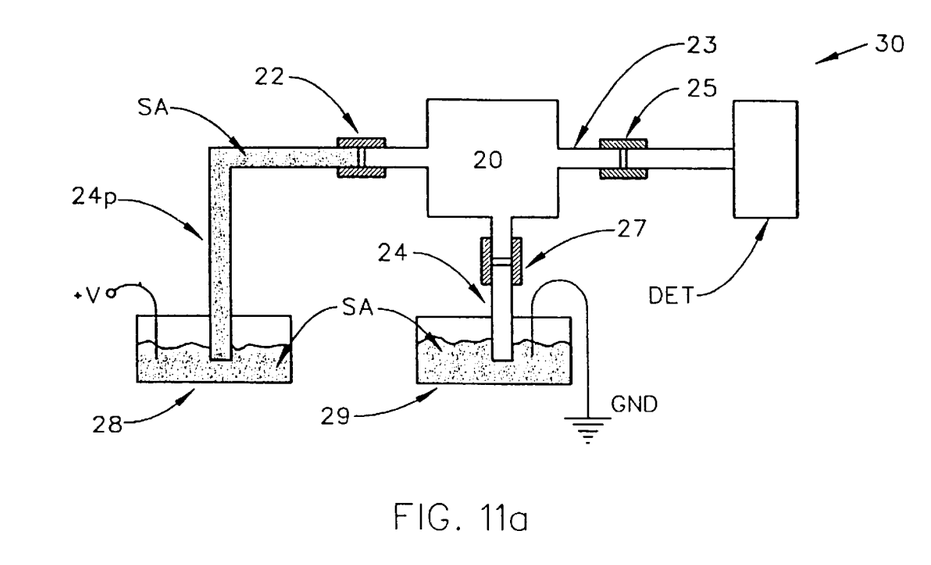
FIG. 11a shows a front elevational view of a modular component system of the present invention.
Figure 11B:
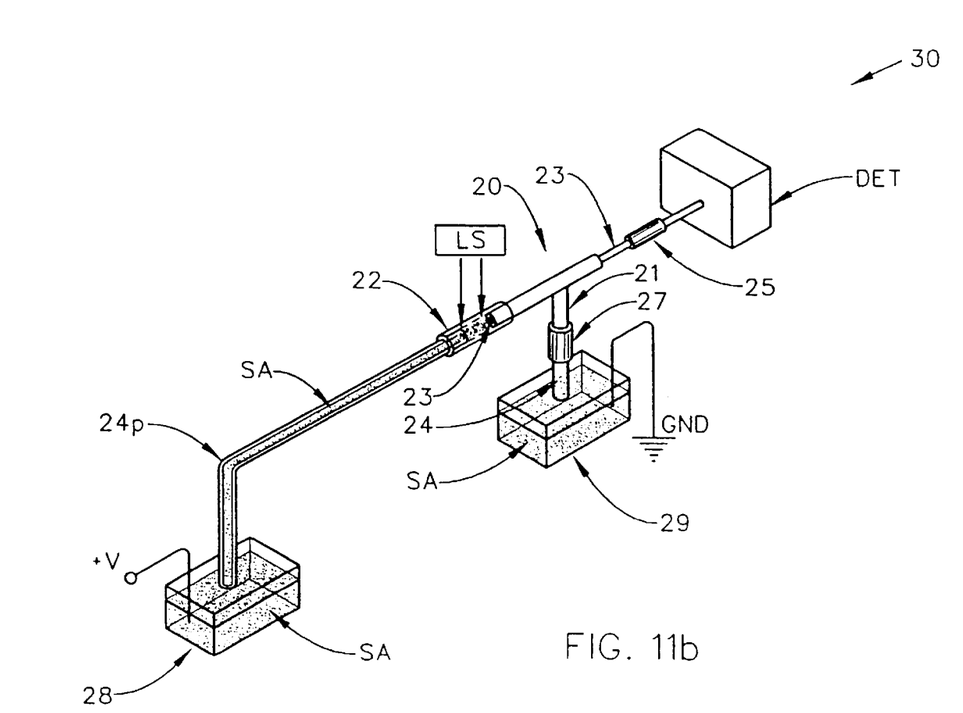
FIG. 11b shows a perspective view of a modular component system of the present invention.
Figure 12A:
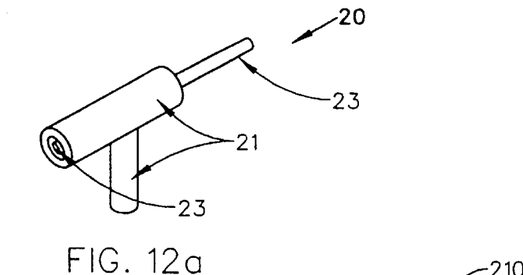
FIG. 12a shows a perspective view of a present invention modular component system fiber optic means containing modular component.
Figure 12B:
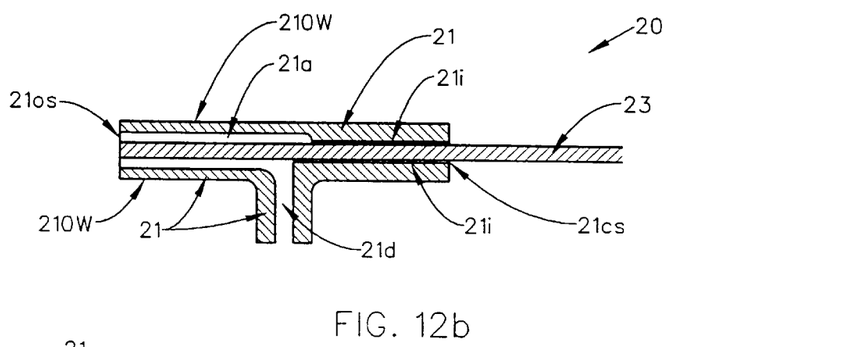
FIG. 12b shows a side cross-sectional view of a present invention modular component system fiber optic means containing modular component.
Figures 12C, 12D:
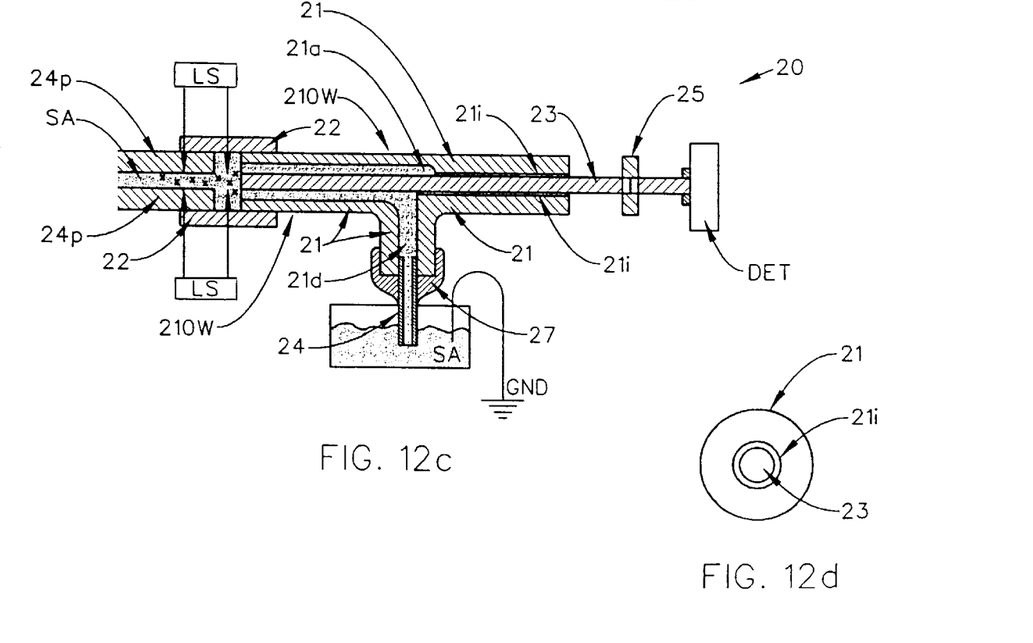
FIG. 12c shows a partial side cross-sectional view of a present invention modular component system shown in FIG. 11b.
FIG. 12d shows a right side elevational view of a present invention modular component system fiber optic means containing modular component of FIG. 12b.

Turning now to FIGS. 11a and 11b, it should be appreciated that they show a variation on the system of FIG. 2. In particular, FIGS. 11a and 11b show, respectively, front elevational and perspective views of another modular component system (30) for use in inducing and measuring sample analyte identifying fluorescence. FIGS. 12a provides a perspective view of a modular component (20) in said modular component system (30). FIG. 12b is a front elevational view of said modular component (20) and shows that it comprises an essentially tubular shaped element (20) with an outer wall (21ow). One end of said essentially tubular shaped element is open (21os) and another end thereof is essentially closed (21cs), and said essentially closed (21cs) end has a fiber optic means (23) secured therewithin, with said fiber optic means (23) projecting from outside said essentially tubular shaped element (20) into said essentially tubular shaped element (20). Said fiber optic means (23) is secured in said essentially closed (21cs) by a securing interface means (21i). It is indicated by FIGS. 12a, 12b and 12c that the end of said fiber optic means (23) which projects into said essentially tubular shaped element (20) is in a common vertical plane, (as shown), which is essentially flush with the open end of the essentially tubular shaped element (20). While this is the preferred embodiment, the present invention includes embodiments wherein the fiber optic means (23) extends into the space bounded by the outer wall (21ow) of the essentially tubular shaped element (20) to least a majority of the length between the open (21os) and essentially closed (21cs) ends thereof. This can include the embodiment wherein said fiber optic means (23) extends beyond the open end (21os) of the essentially tubular shaped element (20). Continuing, an annular space (21a) is formed inside said essentially tubular shaped element (20) and around said fiber optic means (23), said annular space (21a) formed around said fiber optic means (23) is accessed at a location between said open end (21os) and said essentially closed end (21cs) of said essentially tubular shaped element (20), by an annular space accessing means (21d). FIG. 12c shows a partial front elevational view of said modular component system (30) as shown in FIGS. 11a and 11b, and FIG. 12d shows a right side elevational view. Said open end (21os) of said essentially tubular shaped element (20) is, during use, connected to a source, (see identifier (28) in FIG. 11b), of sample analyte (SA) containing solution by way of an essentially transparent essentially tubular connection means (22), such that during use, sample analyte (SA) containing solution is caused to be continuously present in said essentially transparent essentially tubular connection means (22), in said annular space, and in said annular space access means. Essentially transparent essentially tubular connection means (22) can be a separate element or continuous with the essentially tubular shaped element (20). Sample analyte fluorescence (X X X) is then caused to occur by the application of energy (LS) to sample analyte(s) (SA) in said sample analyte containing solution present within said essentially transparent essentially tubular connection means (22), with said fluorescence inducing energy (LS) being entered through said essentially transparent essentially tubular connection means (22). Note, as demonstrated in FIG. 12c, that fluorescence inducing energy (LS) can be entered from essentially any directing, (eg. from the top, bottom and into and out of the page etc.), into said essentially transparent essentially tubular connection means (22). Said produced fluorescence (X X X) is then caused to be transmitted to a detector system (DET) via said fiber optic means (23) outside said modular component (20). (Note that fiber optic means (23) can be spliced into an extra length of fiber optic means by coupler (25) as necessary to reach the detector means (DET), or said fiber optic means (23) can independently be of a length sufficient to reach said detector means (DET)). It is specifically noted that the fiber optic means (23) is oriented axially within said essentially tubular connection means (22), and that the annular space (21a) is preferably of an essentially constant cross-sectional dimension along the length thereof within said essentially tubular shaped element (20).

FIGS. 11a and 11b show that the presently described modular component system (30) for use in inducing and measuring sample analyte identifying fluorescence (X X X) typically further comprises a sample solution containing system source (28) of sample analyte(s) and a sample solution receiving system (29). In use sample analyte(s) (SA) containing sample solution present at said source of sample analyte(s) (28) is caused to be continuous with a sample analyte (SA) containing sample solution present in said sample solution receiving system (29). In use an electric potential, (eg. (+V) with respect to ground (GND)), is applied between said sample analyte (SA) containing solution in said sample solution containing system source (28) of sample analyte and said sample solution present in said sample solution receiving system (29), with the result being that sample analyte(s) (SA) are caused to migrate through said modular component system (30) under the presence of a resulting electric field.

FIGS. 11a, 11b, and 12c also show connectors (25) and (27) for interconnecting said essentially tubular shaped element modular component (20) in said modular component system (30), a means for accessing (24) said sample solution receiving system (29), and a means for accessing (24p) the sample solution containing system source (28) of sample analyte.

The identifier (21) in FIGS. 12a, 12b, 12c and 12d is present to indicate that the presently discussed modular component essentially tubular shaped element modular component (20) is preferably, though not necessarily, of a one-piece construction.

It is noted that the essentially transparent essentially tubular connection means (22) shown best in FIGS. 11b and 12c must be of a material which allows energy transport therethrough in use. Suitable, but not limiting materials include quartz and fused silica.

Methods of producing and accessing for analysis, sample analyte identifying fluorescence utilizing the modular system of FIGS. 11a, 11b, 12a–12d were described in the Disclosure of the Invention Section.

A preferred source of sample analyte(s) fluorescence inducing energy (LS) again involves the use of lasers and energy is caused to be entered through said essentially transparent essentially tubular connection means (22).

It is to be understood that the terminology source of sample analyte(s) fluorescence inducing energy (LS) is sufficiently broad to include the end of a fiber optic means (LS) which emits sample analyte(s) fluorescence inducing energy. In use, the end of said fiber optic means (LS) can be easily positioned and oriented so as to provide fluorescence inducing energy along a pathway which is other than parallel to a fiber optic means for carrying induced fluorescence to a detector. That is, the sample analyte(s) fluorescence inducing energy generating source can be located at some distance from, for instance, said essentially transparent essentially tubular connection means (22) in FIG. 11b and 12c.

It is again noted that the terminology "essentially tubular" is not to be interpreted to impart any limit other than the presence of a space surrounding wall means. An "essentially tubular" shape can be, for instance, circular in cross-section, or square or rectangular etc. in cross section, and said wall means need not be of an essentially cylindrical shape. The preferred embodiment of the present invention, however, utilizes essentially cylindrical shaped essentially tubular shapes with circular cross-sections.

Finally, it is to be recognized that, as shown in FIG. 2, an axially oriented fiber optic means (3) could be entered through a sealed or sealable opening (8) in a retaining means (9) for said axially oriented system modular component (1), such that said fiber optic means (3) is entered thereto directly in line with said axially oriented system modular component bore (2), wherein retaining means (9) in FIG. 2 provides an axially oriented system component bore accessing means which is the equivalent to the FIGS. 12b and 12c identified annular space (21a) accessing means (21d). The structural configuration in FIGS. 12b and 12c can be interpreted as variations on the structural theme shown in FIG. 2. In effect said FIG. 12b configuration can be considered to be an effective "end cap" to which an axially oriented system modular component, (see the FIG. 2 axially oriented system modular component (1) which has the axially oriented system bore (2) therethrough), is affixed. The essentially transparent essentially tubular connection means (22) in FIG. 12c is the analogical corresponding element to the axially oriented system modular component (1) in FIG. 2. In this light it is to be understood that the essentially tubular shaped element modular component (20) can be totally or partially constructed from fluorescence inducing energy transparent materials, and that the essentially transparent essentially tubular connection means (22) can be at least partially comprised of fluorescence inducing energy opague materials. Also, the essentially tubular shaped element modular component (20) the essentially transparent essentially tubular connection means (22) can be separate elements which are joined as shown in FIG. 12c, or they can be continuous as indicated in FIGS. 1 and 2. When continuous, the boundary between said essentially tubular shaped element modular component (20) the essentially transparent essentially tubular connection means (22) can be indistinct, but an essentially transparent wall through which fluorescence inducing energy is entered is properly considered to be in the essentially transparent essentially tubular connection means (22).

Having hereby disclosed the subject matter of the present invention, it should be obvious that many modifications, substitutions, and variations thereof are possible in light thereof. It is therefore to be understood that the present invention can be practiced other than as specifically described, and should be limited in breadth and scope only by the Claims.

We claim:

1. A method of producing and accessing for analysis, sample analyte identifying fluorescence, comprising the steps of:

a. providing a modular component system for use in inducing and measuring sample analyte identifying fluorescence, said modular component system comprising a modular component of continuous construction, such that said modular component has at least four functionally interchangeable ports therein which each access a common volume within said modular component, said modular component system further comprising at least first and second fiber optic means, present in, respectively, a first and a second of said at least four ports, said first and second ports being oriented other than co-axial with one another; in which modular component, during use, sample analyte containing solution is caused to be continuously present within two of said at least four ports of said modular component which do not have said first and second fiber optic means present therein; such that during use sample analyte fluorescence is caused to occur by the application of energy to sample analyte(s) caused to be present within said modular component, said fluorescence inducing energy being entered via one of said first and second fiber optic means, with produced fluorescence being transmitted by the remaining of said first and second fiber optic means to a detector system, without first passing through any portion of said modular component so as to exit said common volume within said modular component before entering said remaining fiber optic means;

b. causing sample analyte(s) to be continuously present in said modular component system modular component with at least four ports, via two of said at least four ports which do not have said first and second fiber optic means present therein;

c. causing sample analyte(s) fluorescence inducing energy to be entered to said modular component system component with at least four ports via one of said first and second fiber optic means; and d. causing produced fluorescence to be transmitted, via the fiber optic means via which fluorescence producing energy is not entered, to a detector system, without first passing through any portion of said modular component so as to exit said common volume within said modular component before entering said remaining fiber optic means.

2. A method of producing and accessing for analysis, sample analyte identifying fluorescence as in claim 1, in which the step c. act of causing sample analyte(s) fluorescence inducing energy to be entered to said modular component system involves the use of lasers.

3. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof.

4. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being all in a common plane.

5. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being all in a common plane, and projecting at an essentially ninety degree or one-hundred-eighty degree angle with respect to each of the other of said four ports.

6. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports.

7. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports and in which said forth port projects essentially perpendicularly to the plane formed by said three "Tee" shape forming ports which form a common plane.

8. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports and in which said forth port projects essentially perpendicularly to the plane formed by said three "Tee" shape forming ports which form a common plane and in which each of said four ports projects at an essentially ninety degree angle with respect to each of the other of said four ports.

9. A method of producing and accessing for analysis, sample analyte identifying fluorescence as in claim 1, in which the step of providing a modular component system with at least four ports involves a modular component wherein ports, other than said first and second ports, project from said common volume other than coaxially with respect to one another.

10. A method of producing and accessing for analysis, sample analyte identifying fluorescence as in claim 1, in which the step of providing a modular component system with at least four ports involves a modular component wherein said first and second ports project from said common volume other than coaxially with respect to one another, and in which the port in which is present said second fiber optic means, is essentially coaxial with one of said ports which does not have said first or second fiber optic means present therein and in which is present sample analyte(s) containing sample solution.

11. A method of producing and accessing for analysis, sample analyte identifying fluorescence comprising the steps of:

a. providing a modular component system for use in inducing and measuring sample analyte identifying fluorescence, said modular component system comprising a modular component of continuous construction, such that said modular component has at least four functionally interchangeable ports therein which each access a common volume within said modular component, said modular component system further comprising at least first and second fiber optic means, present in, respectively, a first and a second of said at least four ports, said first and second ports being oriented other than co-axial with one another; in which modular component, during use, sample analyte containing solution is caused to be continuously present within two of said at least four ports of said modular component which do not have said first and second fiber optic means present therein; such that during use sample analyte fluorescence is caused to occur by the application of energy to sample analyte(s) caused to be present within said modular component, said fluorescence inducing energy being entered via one of said first and second fiber optic means, with produced fluorescence being transmitted by the remaining of said first and second fiber optic means to a detector system, without first passing through any portion of said modular component so as to exit said common volume within said modular component before entering said remaining fiber optic means, said modular component system for use in inducing and measuring sample analyte identifying fluorescence further comprising a sample solution containing system source of sample analyte(s) and a sample solution receiving system, such that in use said modular component system modular component with at least four ports is caused to be filled with a sample analyte(s) containing sample solution, and such that sample analyte(s) containing sample solution present at said source of sample analyte(s) is caused to be continuous with a sample analyte containing sample solution present in said sample solution receiving system, said continuity being via two of said at least four modular component ports which do not have said first and second fiber optic means present therein; such that in use an electric potential is applied between said sample analyte containing solution in said sample solution containing system source of sample analyte and a sample solution receiving system, such that sample analyte(s) present therein are caused to migrate through said modular component;

b. causing sample analyte(s) to be continuously present in said modular component system modular component with at least four ports, via two of said at least four ports which do not have said first and second fiber optic means present therein;

c. applying an electric potential between sample analyte(s) containing sample solution present in said sample solution containing system source of sample analyte(s) and said sample solution receiving system;

d. causing sample analyte(s) fluorescence inducing energy to be entered to said modular component system modular component with at least four ports via one of said first and second fiber optic means; and e. causing produced fluorescence to be transmitted, via the fiber optic means via which fluorescence producing energy is not entered, to a detector system.

12. A method of producing and accessing for analysis, sample analyte identifying fluorescence as in claim 11, in which the step d. act of causing sample analyte(s) fluorescence inducing energy to be entered to said modular component system modular component involves the use of lasers.

13. A method of producing and accessing for analysis, sample analyte identifying fluorescence as in claim 11, in which the step of providing a modular component system with at least four ports involves a modular component in which four ports are oriented in an essentially cross shape, with means for entry of sample analyte present at two ports thereof.

14. A method of producing and accessing for analysis, sample analyte identifying fluorescence as in claim 11, in which the step of providing a modular component system with at least four ports involves a modular component in which four ports are oriented in an essentially cross shape, with means for entry of sample analyte present at two ports thereof, said four ports being all in a common plane.

15. A method of producing and accessing for analysis, sample analyte identifying fluorescence as in claim 11, in which the step of providing a modular component system with at least four ports involves a modular component in which four ports are oriented in an essentially cross shape, with means for entry of sample analyte present at two ports thereof, said four ports being all in a common plane, and projecting at an essentially ninety degree or one-hundred-eighty degree angle with respect to each of the other of said four ports.

16. A method of producing and accessing for analysis, sample analyte identifying fluorescence as in claim 1, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports.

17. A method of producing and accessing for analysis, sample analyte identifying fluorescence as in claim 11, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports and in which said forth port projects essentially perpendicularly to the plane formed by said three "Tee" shape forming ports which form a common plane.

18. A method of producing and accessing for analysis, sample analyte identifying fluorescence as in claim 11, in which the step of providing a modular component system with at least four ports involves a modular component in which four ports are oriented in an essentially cross shape, with means for entry of sample analyte present at two ports thereof, said four ports being oriented such that three ports are in an essentially "tee" shape, with a forth port projecting out of a plane formed by said essentially "tee" shape forming three ports and in which said forth port projects essentially perpendicularly to the plane formed by said three "Tee" shape forming ports which form a common plane and in which each of said four ports projects at an essentially ninety degree angle with respect to each of the other of said four ports.

19. A method of producing and accessing for analysis, sample analyte identifying fluorescence as in claim 11, in which the step of providing a modular component system with at least four ports involves a modular component wherein ports, other than said first and second ports, project from said common volume other than coaxially with respect to one another.

20. A method of producing and accessing for analysis, sample analyte identifying fluorescence as in claim 11, in which the step of providing a modular component system with at least four ports involves a modular component wherein said first and second ports project from said common volume other than coaxially with respect to one another, and in which the port in which is present said second fiber optic means, is essentially coaxial with one of said ports which does not have said first or second fiber optic means present therein and in which is present sample analyte(s) containing sample solution.

21. A method of producing and accessing for analysis, sample analyte identifying fluorescence, comprising the steps of:
  a. providing a modular component system for use in inducing and measuring sample analyte identifying fluorescence, said modular component system comprising:
    a. a source of fluorescence inducing energy;
    b. a detector system;
    c. first and second fiber optic means; and
    d. a modular component with at least four functionally interchangeable ports therein, which ports each access a common volume within said modular component;
  said modular component being of continuous construction and having said first and second fiber optic means present in, respectively, a first and a second of said at least four ports, which first and second ports project from said common volume in directions which are other than coaxial with respect to one another; said modular component further having another of said four ports, which does not have a fiber optic means present therein oriented essentially coaxial said port which has said second fiber optic means present therein; each of said at least four modular component ports being functionally adaptable to containing either a fiber optic means or sample analyte(s) containing solution;
  said source of fluorescence inducing energy being functionally connected to said first fiber optic means and said second fiber optic means being functionally connected to said detector system;
  said modular component system for use in inducing and measuring sample analyte identifying fluorescence further comprising:
    e. a sample solution containing source of sample analyte(s);
    f. a sample solution receiving system; and
    g. a means for providing electric potential;
  such that, in use, sample analyte(s) containing sample solution present at said source of sample analyte(s) is caused to be continuous with a sample analyte(s) containing sample solution present in said sample solution receiving system, said continuity being via sample analyte(s) containing sample solution present in
  said two of said at least four modular component ports which do not have said first and second fiber optic means present therein, and said common volume;
  such that, in use, an electric potential provided by said means for providing electric potential is applied between said sample analyte(s) containing solution in said sample solution containing system source of sample analyte and that in said sample solution receiving system, such that sample analyte(s) in said sample solution are caused to migrate through said modular component system modular component;

such that, in use, said source of fluorescence inducing energy is caused to provide energy to sample analyte(s) caused to be present within said modular component common volume thereby causing fluorescence to be induced;

and such that, in use, at least some of said induced fluorescence is intercepted and transmitted by the other of said first and second fiber optic means to said detector system, without first passing through any portion of said modular component so as to exit said common volume within said modular component before entering said remaining fiber optic means;

b. causing sample analyte(s) to be continuously present in said modular component system modular component with at least four ports, via two of said at least four ports which do not have said first and second fiber optic means present therein;

c. applying an electric potential between sample analyte(s) containing sample solution present in said sample solution containing system source of sample analyte(s) and said sample solution receiving system;

d. causing sample analyte(s) fluorescence inducing energy to be entered to said modular component system modular component with at least four ports via said first fiber optic means; and e. causing induced fluorescence to be transmitted, via said second fiber optic means, to said detector system.

22. A method of producing and accessing for analysis, sample analyte identifying fluorescence, comprising the steps of:

a. providing a modular component system for use in inducing and measuring sample analyte identifying fluorescence, said modular component system comprising a modular component of continuous construction having at least four functionally interchangeable ports therein, each of which ports projects from a common volume within said modular component; said modular component further comprising first and second fiber optic means present in, respectively, a first and a second of said at least four ports;

b. causing sample analyte(s) to be continuously present in said modular component system modular component with at least four ports, via two of said at least four ports which do not have said first and second fiber optic means present therein;

c. causing sample analyte(s) fluorescence inducing energy to be entered to said modular component system component with at least four ports via one of said first and second fiber optic means; and d. causing produced fluorescence to be transmitted, via the fiber optic means via which fluorescence producing energy is not entered, to a detector system, without first passing through any portion of said modular component so as to exit said common volume within said modular component before entering said remaining fiber optic means.

23. A method of producing and accessing for analysis, sample analyte identifying fluorescence as in claim 22, wherein the step of providing a modular component system for use in inducing and measuring sample analyte identifying fluorescence involves providing a modular component wherein each of said ports is functionallly adaptable to containing either a fiber optic means or sample analyte(s) containing solution.

24. a method of producing and accessing for analysis, step analyte identifying fluorescence as in claim 22, wherein the sample of providing a modular component system for use in inducing and measuring sample analyte identifying fluorescence involves providing a modular component wherein said first and second ports project from said common volume other than coaxially with respect to one another.

25. A method of producing and accessing for analysis, sample analyte identifying fluorescence as in claim 22, wherein the step of providing a modular component system for use in inducing and measuring sample analyte identifying fluorescence involves providing a modular component wherein the port in which is present said second fiber optic means, is essentially coaxial with one of said ports which does not have said first or second fiber optic means present therein and in which is present sample analyte(s) containing sample solution in use.

26. A method of producing and accessing for analysis, sample analyte identifying fluorescence as in claim 22, wherein the step of providing a modular component system for use in inducing and measuring sample analyte identifying fluorescence involves providing a modular component wherein said first and second ports projects from said common volume other than coaxially with respect to one another, and wherein the port in which is present said second fiber optic means, is essentially coaxial with one of said ports which does not have said first or second fiber optic means present therein and in which is present sample analyte(s) containing sample solution, in use.

* * * * *